United States Patent
Smith (10) Patent No.: US 9,724,443 B2
(45) Date of Patent: Aug. 8, 2017

(54) SYSTEM, METHOD, AND DEVICE FOR DECONTAMINATION

(71) Applicant: Rememdia LC, Salt Lake City, UT (US)

(72) Inventor: Fraser Smith, Salt Lake City, UT (US)

(73) Assignee: Rememdia LC, Salt Lake City, UT (US)

( * ) Notice: Subject to any disclaimer, the term of this patent is extended or adjusted under 35 U.S.C. 154(b) by 67 days.

(21) Appl. No.: 14/684,253

(22) Filed: Apr. 10, 2015

(65) Prior Publication Data
US 2016/0296077 A1    Oct. 13, 2016

(51) Int. Cl.
*A61L 2/28*    (2006.01)
*B08B 7/00*    (2006.01)
*E03C 1/05*    (2006.01)

(52) U.S. Cl.
CPC ............... *A61L 2/28* (2013.01); *B08B 7/0057* (2013.01); *E03C 1/057* (2013.01)

(58) Field of Classification Search
None
See application file for complete search history.

(56) References Cited

U.S. PATENT DOCUMENTS

2008/0031838 A1    2/2008  Bolling
2009/0087028 A1*   4/2009  Lacey ............... G08B 21/245
                                                382/103

FOREIGN PATENT DOCUMENTS

WO    WO 2008/118143 A2    10/2008

OTHER PUBLICATIONS

Davidhazy, The Wraten 18A A problematic filter for reflected ultraviolet photography, Rochester Institute of Technology, https://people.rit.edu/andpph/text-ultraviolet-wratten-18A.html, as accessed Jan. 22, 2015, 5 pages, Rochester, New York.

* cited by examiner

*Primary Examiner* — Kishor Mayekar

(57) ABSTRACT

A system for decontaminating the hands of a person is disclosed having a composition with a marker agent capable of luminescence when exposed to light having a wavelength ranging from approximately 315 to 400 nanometers. The composition is disposed in a container capable of receiving the hands of a person therein such that when the hands of the person are placed in the container the hands of the person are immersed in the composition. A water dispenser is provided that operates in conjunction with a light source adapted to emit radiation having a wavelength ranging from approximately 315 to 400 nanometers. A washing event occurs while light is directed towards the location of the washing event.

8 Claims, 4 Drawing Sheets

SYSTEM, METHOD, AND DEVICE FOR DECONTAMINATION

FIELD OF THE TECHNOLOGY

The present technology relates to methods and systems of cleaning hands and other parts of the body, and more particularly to methods and systems of cleaning the body to rid it of contaminants and other potential hazards adhering to the skin of an individual.

BACKGROUND OF THE TECHNOLOGY AND RELATED ART

At present, there is an ongoing and ever increasing concern over the spread of infectious diseases and other biological or chemical hazards for infection control and/or the control of cross-contamination. Conventionally, persons suspected of being contaminated with chemical and/or biological agents are led into a decontamination tent, trailer, or pod, where they shed their potentially contaminated clothes in a strip-down room. They then enter a wash-down room and are showered. Finally, they enter a drying and re-robing room to be issued clean clothing, or a jumpsuit or the like. Such decontamination procedures are difficult to employ and impractical for routine washing or decontamination like that in a hospital.

Hand-washing in a hospital setting often employs soap and/or an antiseptic agent together with a specific scrubbing protocol. Chemical preparations (other than soap) for hand hygiene can be used, for example, chlorhexidine gluconate (clear/pink solution); iodine based preparations (brown); and aqueous alcoholic solutions (clear), though iodine based preparations have been known to cause skin irritation. For surgical procedures, hand-washing begins at the fingernails, where a nail file and brush from a sterile pack can be used. Scrubbing then occurs in three washing cycles: (a) hands and arms extending to two inches above the elbow; (b) hands and half way up the forearms; and (c) hands only. This follows the principle of washing from a clean area (the hand) in the direction of the less clean area (the arm). Hands should always be held above the level of the elbows at all times in order to prevent dirty water from dripping from the upper arm onto lower sterile areas.

Hospital-acquired infections are a major cause of illness and death, and impose serious economic costs on patients and hospitals. Indeed, health care-associated infections result in an estimated 90,000 deaths each year in the United States. Cross transmission is estimated to cause 40% of certain infections. Pathogens are readily transmitted on the hands of a healthcare worker, and effective hand hygiene substantially reduces this transmission. For decades, hand-washing has been universally accepted as one of the most important measures for preventing transmission of pathogens in health-care facilities and other community settings. However, compliance with established hand-washing guidelines remains poor. It is therefore necessary to improve the methods and systems of decontamination before a surgery or any other event where the spread of a chemical or biological hazard is possible.

SUMMARY OF THE INVENTION

In light of the problems and deficiencies inherent in the prior art, the present invention seeks to overcome these by providing a system for decontaminating the hands of a person. In accordance with one aspect of the technology, a system is provided comprising a composition comprising an agent capable of luminescence when exposed to radiation having a wavelength ranging from approximately 315 to 400 nanometers, wherein the composition is located in a container capable of being disposed about the hands of the person. A water dispenser is provided that is adapted to communicate water from a water source to the hands of a person. In addition, a light source is provided that is operative with the water dispenser. The light source is oriented to emit light in a direction of the hands of the person when disposed beneath the water dispenser and is actuatable to emit radiation sufficient to cause the agent disposed about the hands of the person to luminesce.

In accordance with an additional aspect of the technology, a device for decontaminating the hands of a person is disclosed comprising a water dispenser adapted to communicate water from a water source to the hands of a person comprising a base, a hollow body, and a water discharge outlet. A light source is provided that is operative with the water dispenser. The light source is oriented to emit light in a direction of the hands of the person when disposed beneath the water dispenser, wherein the light source is actuatable to emit radiation sufficient to cause the agent disposed about the hands of the person to luminesce. In addition, a sensor is provided that is operative to automatically actuate the water dispenser and light source upon detecting the presence of the person.

In accordance with another aspect of the technology, a method of decontaminating the hands of a person is provided comprising the step of placing the hands of the person proximate to a water dispenser and light source, said water dispenser being adapted to communicate water from a water source to the hands of a person and said light source being adapted to emit light in a direction of the hands of the person when the hands are disposed beneath the water dispenser and wherein the light source is actuatable to emit radiation sufficient to cause a luminescent marker disposed about the hands of the person to luminesce. The method further comprises visually inspecting the hands of the person while the hands are placed within the light emitted from the light source for traces of the luminescent marker and receiving water from the water dispenser and washing the hands of the person while maintaining the hands in the light emitted from the light source.

BRIEF DESCRIPTION OF THE DRAWINGS

The present technology will become more fully apparent from the following description and appended claims, taken in conjunction with the accompanying drawings. Understanding that these drawings merely depict exemplary aspects of the present technology they are, therefore, not to be considered limiting of its scope. It will be readily appreciated that the components of the present technology, as generally described and illustrated in the figures herein, could be arranged and designed in a wide variety of different configurations. Nonetheless, the technology will be described and explained with additional specificity and detail through the use of the accompanying drawings in which:

DETAILED DESCRIPTION OF EXEMPLARY ASPECTS OF THE TECHNOLOGY

The following detailed description of exemplary aspects of the technology makes reference to the accompanying drawings, which form a part hereof and in which are shown, by way of illustration, exemplary aspects in which the technology may be practiced. While these exemplary aspects are described in sufficient detail to enable those skilled in the art to practice the technology, it should be understood that other aspects may be realized and that various changes to the technology may be made without departing from the spirit and scope of the present technology. Thus, the following more detailed description of the aspects of the present technology is not intended to limit the scope of the technology, as claimed, but is presented for purposes of illustration only and not limitation to describe the features and characteristics of the present technology, to set forth the best mode of operation of the technology, and to sufficiently enable one skilled in the art to practice the technology. Accordingly, the scope of the present technology is to be defined solely by the appended claims. The following detailed description and exemplary aspects of the technology will be best understood by reference to the accompanying drawings, wherein the elements and features of the technology are designated by numerals throughout.

The present technology describes systems, devices, and methods for improved decontamination. Previous decontamination practices, including those related to hand washing, fall short of the acceptable removal of biological or chemical hazards. Several publications have described the use of soap or other disinfectant solutions that can change color or physical property as a function of time after it has been dispensed on to the hands. See, for example, U.S. Pat. No. 7,053,029, U.S. Patent Publication Nos. 2006/0264346, 2005/0233919, 2005/0233918, 2005/0090414. Other publications (U.S. Pat. Nos. 5,900,067 and 6,524,390 and U.S. Patent Publication No. 2012/0214879) introduce a fluorescent agent into the soap solution and examine the hands after rinsing to see whether any fluorescence is left behind to assure the hands no longer have soap left over. These methods, however, suffer from a soap-application bias and inefficiencies in the washing process. When the person that applies the soap to the hands and proceeds to wash his or her hands, the person may not evenly distribute soap across the hands or to all areas of the hands that may have a biological or chemical hazard present. Indeed, the places where biological or chemical hazards may persist on the hands of a person may be the hardest places to deliver the soap. In other words, the same method that a person uses to remove the soap is likely used to apply the soap, both of which result in inadequate coverage about the hands of the person. A method that begins with hands that are open with the fingers and thumb spread apart and covered with a liquid having a marking agent (e.g., a fluorescing compound) minimizes the soap-application bias.

In addition, the action of washing hands and then placing them under a remote light source intended to cause residual luminescent compounds on the hands to luminesce becomes cumbersome and time consuming which can result in users skipping important washing procedures or failing to observe the presence of residual luminescence. Light sources that are directed at the area used for washing, however, create an environment where the user can observe the presence of residual luminescence in real-time during a washing event. It is believed that this feature saves time and helps produce an increased level of decontamination on the part of the user. Moreover, with the light source associated directly with the location of the washing event, methods and timing constructs can be employed to train individuals to continue the washing event until all (or an acceptable level) of the luminescence is removed from the hands without having to stop the washing event, move to a light source, and begin a new washing event if residual luminescence is not removed to an acceptable level.

It is intended that the present technology be operable with different types of functional attachments or components and compositions with the end result of improved systems, devices, and methods for decontamination. Bearing that in mind, aspects of the technology can be broadly described as a system for decontaminating the hands of a person, comprising a composition having a marker agent capable of luminescence when exposed to light. The composition is disposed, for example, in a container capable of receiving the hands of a person therein such that when the hands of the person are placed in the container the hands of the person are fully immersed in the composition. The technology further utilizes a water dispenser adapted to communicate water from a water source to the hands of a person and operates in conjunction with a light source adapted to emit radiation having a wavelength ranging, for example, from approximately 315 to 400 nanometers. The light path of the light source is oriented such that it illuminates the area where the washing event takes place.

As noted above, the technology described herein provides improved systems and devices for, compositions for, and methods of improved hand hygiene, washing or contact time, hand hygiene techniques, or both, using a luminescent indicator (or marking agent) with an improved application technique and device for incentivizing improved hand hygiene. As used herein, the term "luminescence" may pertain to fluorescence, phosphorescence, and chemiluminescence, as well as to selective absorbance of predefined wavelength regions of the electromagnetic spectrum, such as infrared (IR) and near infrared (NIR). A luminescent composition is one which emits (or absorbs) light, which is not derived from the temperature of the emitting body.

Luminescent compositions in accordance with the present technology may include a selected luminescent marker, an antimicrobial agent or cleansing agent, and/or an ionizing agent. An ionizing agent may cause an aspect of a luminescent composition to exhibit luminescence over a predetermined indicatory period. Typically, the form of the luminescent composition may be a solution or a gel, although other non-limiting examples of luminescent composition forms may include a cream, a lotion, a solution, a liquid, a soap, a shampoo, a jelly, an aerosol, a powder, a foam, or one or more constituent elements thereof.

A selected luminescent marker may include, but is not limited to, coumarinic compounds, such as coumarin, 7-hydroxy coumarin (umbelliferone), 7-hydroxy-4-methylcoumarin (4-methylumbelliferone, or 4-MU), or 6-glucoside umbelliferone (esculin), 7-hydroxy-4 (trifluoromethyl) coumarin, and aromatic compounds having at least one fused ring (benzene derivatives). An aromatic compound with two or more fused rings (e.g. naphthalenes, anthracenes) may be used to provide a selected luminescent marker, which is strongly fluorescent when ionized in a solvent, acid, or base, for example, a selected ionizing agent. A suitable selected luminescent marker also may be a solvent-dependent or pH-dependent (environmentally sensitive) fluorophors, such as pyrene-1-sulfonyl-chloride, pyrene-8-hydroxy-1,4,6-trisulfonyl chloride, quinine and its salts, and quinoids including quinolines and quinines. Carbazol may be used as a selected luminescent marker, which provides a persistent luminescent indicator, in the presence of sodium hydroxide.

An example ionizing agent may be a solvent, acid, or base. In base form, a selected ionizing agent may comprise at least one alkalizing agent, which alkalizing agent may serve as a source of ammonium ions, ammonia, or both. An alkanolamide may be used as an alkalizing agent, as may any other alkalizing agent known in the art. Non-limiting examples of an alkanolamide include monoethanolamine (MEA), diethanolamine (DEA), triethanolamine (TEA), monopropanolamine (MPA), dipropanolamine (DPA), tripropanolamine (TPA), 2-amino-2-methyl-1,3-propanediol (AMPD), 2-amino-2-methyl-1-propanol (AMP), and 2 amino-2-hydroxymethyl-1,3-propanediol (THAM) and guanidium salts. Alkanolamines, alkylamines, alkali hydroxides, and alkali carbonates also may be used as other volatile bases such as, without limitation, pyridine, piperazine, amino methylpyridines, amino ethyl pyridines, amino methoxy pyridines, amino ethyl pyrrolidines, and amino methyl piperazines.

Other non-limiting examples of ammonium sources include ammonium carbonate, ammonium carbamate, ammonium hydrogen carbonate, ammonia, and mixtures thereof, although ammonium chloride, ammonium sulphate, ammonium nitrate, ammonium phosphate, ammonium acetate, ammonium hydroxide, and mixtures thereof, also may be used as ammonium sources. In selected aspects, a composition including a selected luminescent marker may not exhibit luminescence until at least partly mixed with a selected ionizing agent, providing a two-phase luminescent composition, though this aspect is not required in all aspects of the technology.

In yet another aspect of the technology, amine-reactive fluorophors may be used in the composition, which exhibit a very low level of fluorescence until conjugated with an amine. Once conjugated, these fluorophors can become very brightly fluorescent. Non-limiting examples of amine reactive reagents include fluorescamine, o-phthalaldehyde, 4-dimethylaminocinnamaldehyde, dansyl chloride, 8-anilino-1-napthalenesulfonic acid (and its salts), 4-chloro-7-nitrobenzofurazan, fluorescein isothiocyanate, zinc-complexed ninhydrin, 1,2-indanedione, 5-methylthioninhydrin, and 1,8-diazafluoren-9-one. Of these, fluorescamine and dansyl chloride fluoresce strongly in UV light after conjugation with an amine, while the others fluoresce optimally in longer wavelengths ranging from blue (450 nanometers) to green (530 nanometers). In some aspects, UV detectors using UV LEDs may be used to measure luminescence. In other aspects of the technology, longer wavelength light sources, such as blue and green may be used. To humanly see or to electronically measure luminescence in blue or green light, a color filter that blocks the excitation light but transmits the emission light, may be used.

In certain aspects of the technology, a suitable gel may include a diluent, such as water, in which is dispersed a gellant or a thickener, for example, a hydroxyethyl cellulose (HEC) material, a hydroxypropyl cellulose (HPC) material, an ethyl hydroxyethyl cellulose (EHEC) material, a hydroxypropyl methylcellulose (HPMC) material, or a polyamide ester material. In one non-limiting example, a suitable carrier formulation may be a gel including water as a diluent, and between about 0.5% to about 1.0% w/w of hydroxypropyl cellulose (HPC), having a viscosity of between about 4,000 centipoise to about 6,500 centipoise (as may be referenced by the apparent viscosity of a 2% HPC aqueous solution at 25° C.).

Alcohol-based compounds may be used in certain aspects, which may improve hand hygiene because they tend to require less time to use, act faster, may be less irritating, and may contribute to sustained improvement in compliance associated with decreased infection rates. Alcohol may have a broad antimicrobial spectrum, in that it can be active against many bacteria and clinically important viruses, yeasts, and fungi. As a result, a suitable selected antimicrobial agent for a present luminescent composition embodiment may be an alcohol. Antimicrobial efficacy can be achieved with ethanol (about 60% to about 85%), isopropanol (about 60% to about 80%), or n-propanol (about 60% to about 80%). Ethanol at high concentrations (e.g., about 95%) may be an effective treatment against naked viruses, whereas n-propanol may be effective against the resident bacterial flora. The combination of alcohols may have a synergistic effect. However, aspects of the present technology also may be used in a water-based, liquid soap, containing no alcohol so long as the luminescent composition provides an indicator as to what portions of the hand have not be effectively washed.

In a preferred aspect of the technology, a luminescent marker (i.e., marker agent) is used that luminesces when subject to wavelengths of light in the near UV spectrum or approximately 315 to 400 nanometers. Luminescent markers that emit light while under wavelengths of light in the mid (290-315 nm) or far (190-290 nm) UV fields are less desirable because they may cause skin or eye burns. While aspects of the technology direct the field of UV light away from a user's eyes and/or ensure that the light path of the light is not directed at a user's eyes, mid or far UV is still discouraged for use with the current technology in an effort to avoid inadvertent exposure.

Figure 1:
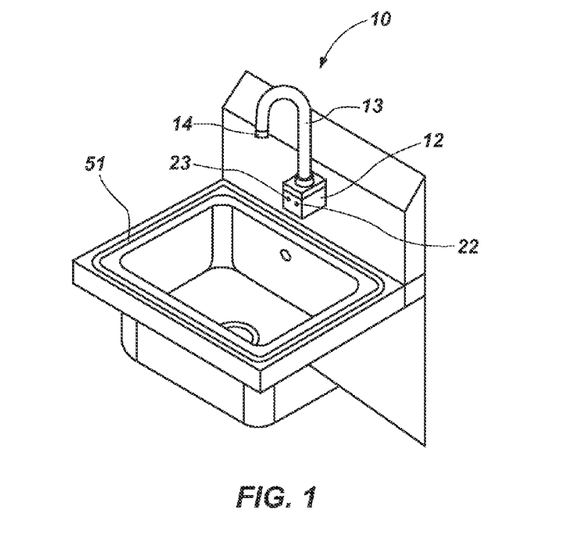
FIG. 1 is a perspective view of a water dispenser and wash basin in accordance with one aspect of the technology.

With reference now to the drawings and specific reference to FIG. 1, in accordance with one aspect of the technology, a water (or other fluid) dispenser 10 is disclosed and is adapted to communicate water from a water source to the hands 50 of a person. The water dispenser 10 is placed near a washbasin 11 wherein a person may place their hands 50. In certain aspects of the technology, prior to placing the hands 50 of the person in the washbasin 11, the person applies a composition capable of luminescence about his or her hands 50. One method of effectively doing so comprises placing his or her hands 50 in a container having a composition capable of luminescence. The fingers and hands 50 of the person should be fully extended and the hands 50 should be fully immersed in the composition for a predetermined period of time to maximize contact of the composition with the hands 50 of the person. For example, in one aspect the user fully immerses his or her hands 50 in the composition for 30 seconds. In an additional aspect, a sensor is placed about the container so as to detect the presence of the hand of the person within the container as well as the amount of the composition within the container. The sensor is configured to provide a visual or audible indicator when the persons hand has been immersed in the composition for the predetermined period of time. While 30 second has been referenced above, it is understood that many different time periods may be used as suits a particular application and when used with a particular composition. In a preferred aspect of the technology, the hands, or other body part or device (e.g., boots, gloves, etc.) are fully immersed in the composition for at least 20 seconds.

Figure 2:
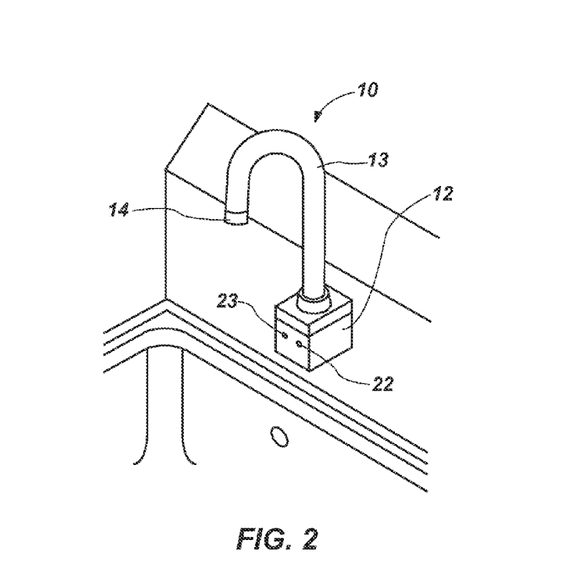
FIG. 2 is a close-up view of a water dispenser in accordance with one aspect of the technology.
Figure 3:
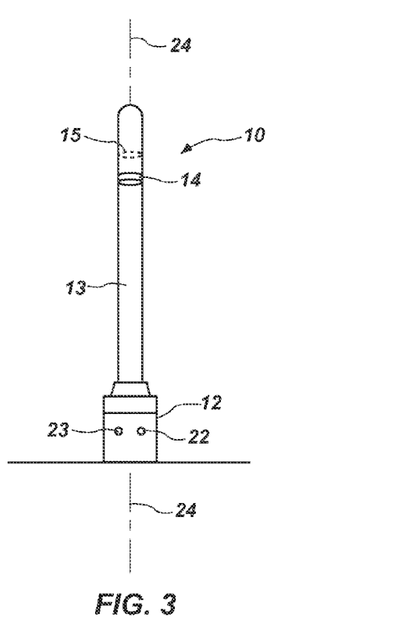
FIG. 3 is a front view of a water dispenser in accordance with one aspect of the technology.

In one aspect of the technology, the water dispenser 10 is disposed about the washbasin 11 so as to provide an environment where the user may place his or her hands 50 beneath the discharge outlet 14 of the dispenser 10 and wash the composition from his or her hands 50 while concurrently observing the presence of any luminescent material that is or may remain on the hands 50 of the user. With reference to FIGS. 1 and 2, the water dispenser 10 is disposed atop a washbasin 11 and comprises a base 12, a hollow body 13 acting as a water conduit, and a water discharge outlet 14. The water dispenser 10 is operatively coupled to a power source. The power source is operatively coupled and configured to activate a light source 15, a sensor 16, and an associated valve system. The light source 15 is disposed about the water dispenser 10 and, in accordance with one aspect of the technology, is adapted to emit light having a wavelength ranging from approximately 315 to 400 nanometers. The light source 15 is positioned such that a direction of the light emitted from the light source 15 is substantially similar to the direction of water emanating from the water discharge outlet 14. In this manner, the user may concurrently wash his or her hands 50 and view luminescent material that may remain on the hands 50 as part of the composition. In one aspect of the invention, the light source 15 is disposed about the exterior of the water discharge outlet 14. Non-limiting examples of light sources include light emitting diodes (LEDs), incandescent bulbs, or fiber optics coupled to remote LEDs or bulbs but having an end point disposed about the water discharge outlet 14. In another aspect, the light source 15 is secured to an exterior of the discharge outlet 14 or an interior of the discharge outlet 14. In yet another aspect, the light source 15 is disposed about the base 12 or sides of the washbasin 11 with the light source 15 directed at the area intended for washing.

Figure 6:
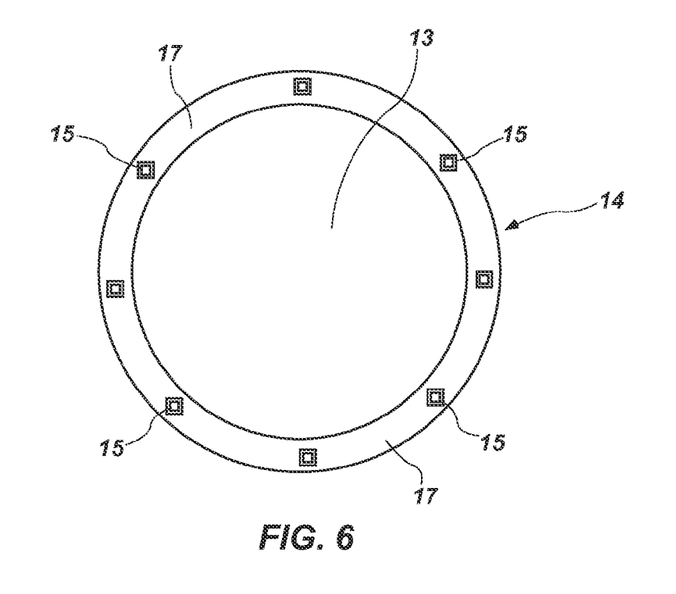
FIG. 6 is a bottom view of a discharge outlet of a water dispenser in accordance with one aspect of the technology.

With specific reference to FIG. 6, the discharge outlet 14 may be configured with an annular member 17 housing one or more light sources 15 directing light emissions downward (i.e., in the direction of the water discharge). In an aspect where the light sources 15 comprise LED's or incandescent bulbs, the light sources 15 are coupled to an energy source within the base 12 of the dispenser 10. In an aspect where the light source 15 comprises a fiber optic cable, the fiber optics terminate at the discharge outlet 14 and are positioned such that light emanating from the fiber optic cables is directed downward in the direction of the water discharge. The fiber optic cables may be placed internally within the water dispenser 10 and directed to an originating light source either in the base 12 or some other location as suits a particular purpose. While specific placements and combinations of light sources are described herein, one of ordinary skill in the art will recognize the various permutations without departing from the scope of the technology (e.g., LED power source may be placed in locations other than the base, light sources placed to direct light laterally toward the water source and so on).

Figure 4:
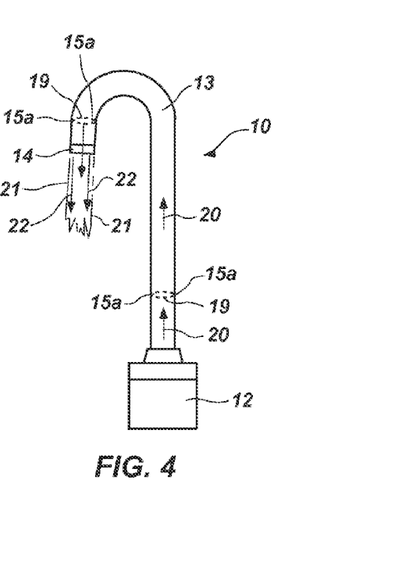
FIG. 4 is a side view of a portion of a water dispenser in accordance with one aspect of the technology.
Figure 5:
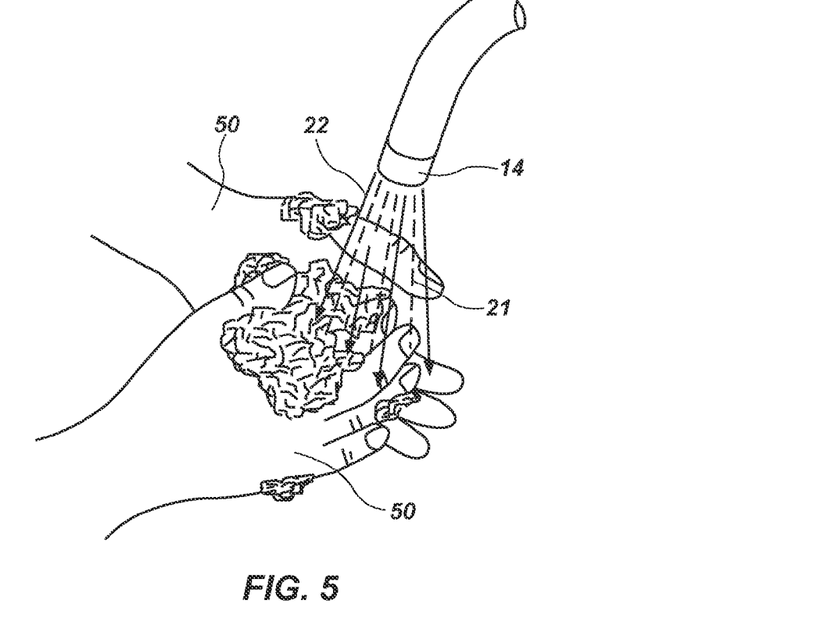
FIG. 5 is a perspective view of a hand-washing event in accordance with one aspect of the technology.

In another aspect of the technology, as shown in FIG. 4, a light source 15a is disposed within the hollow body 13 of the water dispenser 10 and is operative to propagate light into the water stream prior to its discharge from the water dispenser 10. In one non-limiting example, a UV LED (or plurality of UV LEDs) is disposed about an internal perimeter 19 of the hollow body 13 and configured to propagate light when a solenoid valve is opened. Once activated, the light source 15a propagates light into the water stream (shown at 20). As the water stream is discharged from the discharge outlet 14, the outer perimeter 21 of the water stream acts as a conduit or a quasi-fiber optic cable channeling a of the UV light downward with the stream of water. In this manner, light is directed to the location of the hand-washing event and further enhances the ability of the user to observe luminescence on his or her hands 50 during the washing event. In one aspect of the technology, the flowrate of the water is configured to minimize turbulence in an effort to decrease scattering of the light within the stream of water.

In accordance with one aspect of the technology, a sensor, operative to automatically operate the water dispenser 10 and light source 15, is located in the base 12 of the water dispenser 10. The sensor comprises a signal emitter 22 and a signal detector 23 disposed intermediate the bottom of the base 12 and the discharge outlet 14. The emitter 22 and detector 23 are disposed proximate the longitudinal centerline 24 of the hollow body 13. The emitter 22 and detector 23 each have a field of view symmetrical about an axis that is parallel to a centerline 24 of the discharge outlet 14. In this manner, placement of the hands 50 and operation of the water dispenser 10 in conjunction with the light source 15 is optimized. In one aspect, the washbasin 11 is attached to a wall 52 and water dispenser 10 is connected to a water supply line. The water supply line includes a valve operable by a solenoid or other type of actuator or actuating mechanism and is connected to a mixing valve which mixes hot and cold water, which is then fed to the supply line. The solenoid (or other actuator) is controlled by signals from signal emitter 22 and signal detector 23. Electrical connections for the power supply and the control sensors are provided through an electric cable.

In one aspect of the technology, the sensor comprises a timer and is adapted to activate the light source 15 upon the detection of the presence of a user for a predetermined period of time and dispense water from the water dispenser 10 at the termination of the predetermined period of time, which may be referred to as a pre-washing examination period. In this manner, after the user has applied the composition, he or she places the hands 50 in the washbasin 11 and examines the hands 50 to ensure they are appropriately covered with the composition by observing the residual luminescence. In the event they are not appropriately covered, the user may rub the hands 50 together to further apply the composition or move the hands 50 away from the sensor and back to the container housing the composition. In one non-limiting example, the pre-washing examination period ranges from five to ten seconds. At the termination of the predetermined period of time, the solenoid valve is actuated and water from the water supply is provided to the water dispenser 10 and through the discharge outlet 14. In the event the hands are appropriately and sufficiently covered with the composition upon initial inspection, the predetermined time may be overridden by the user and the water supply activated. In one example, this may be accomplished by removing the hands from the sensor and then within a given time period (e.g., 1-2 seconds) immediately returning the hands to the sensor, which then activates the water supply.

In one aspect of the technology, the timer is configured to dispense water for a predetermined period of time. In one non-limiting example, the timer dispenses water for a period ranging from 45 to 60 seconds after-which the solenoid valve is closed. The light source 15 however can be caused to remain active to permit the user to visually inspect his or her hands 50 for any residual luminescent material. The solenoid valve remains closed for a period ranging from 10 to 15 seconds, for example. If the sensor detects that the user's hands 50 remain in position for washing at the end of the period, the solenoid valve is again opened so the user may continue to scrub his or her hands 50. This process is repeated until the user removes his or her hands 50 from the washbasin 11. Once the user removes his or her hands 50 from the washbasin 11, the light source 15 is deactivated and the solenoid valve is (or remains) closed. It is understood and contemplated herein, that the timer and operation of the light source 15 and water discharge can be configured with a variety of different operation protocols. For example, in one aspect of the technology the light source 15 may be activated initially at the same time as the water dispenser 10 (i.e., without a pre-examination period). Or, as noted above, the light source 15 may be activated prior to water being discharged into the washing area.

Figure 7:
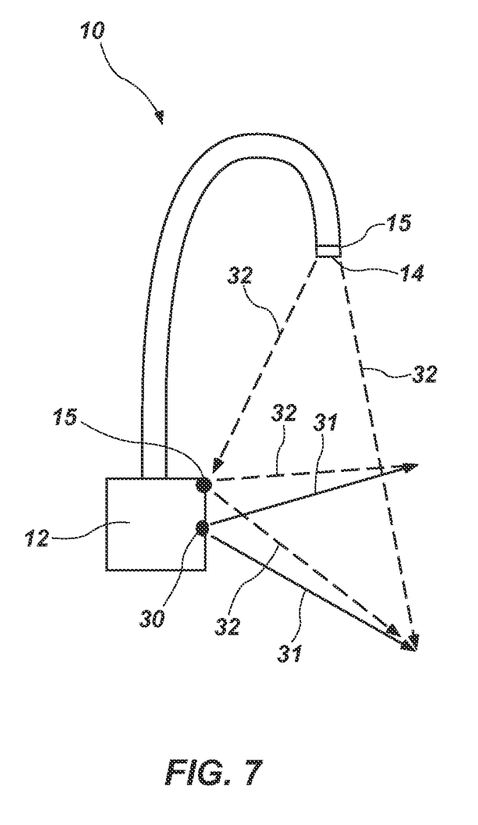
FIG. 7 is a side view of a water dispenser in accordance with one aspect of the technology.

While reference is made herein to a sensor located in the base 12 of water dispenser 10, it is understood that the sensor may be positioned in other locations so long as it functions to define a washing area where the user may place his or her hands 50 and concurrently wash the hands 50 while viewing the presence of luminescent material on the hands 50 of the user. With reference generally to FIG. 7, a sensor 30 is disclosed having a field of view 31. The field of view 31 comprises the area where, when the hands 50 of the user are placed, a signal is sent to operate the light source 15 and solenoid valve. The light path 32 of the light source 15 is coincident, to a certain extent, with the field of view 31 of sensor 30. While FIG. 7 discloses two light sources 15, it is understood that one or more light sources may be used in connection with the present technology. Herein, the central washing area is defined by the area that is coincident with the field of view 31 of the sensor 30, the light path 32 of the light source 15, and the flow path of water (or some water solution) emanating from the discharge outlet 14.

In an additional aspect of the technology, the washbasin 11 comprises a material that is substantially not luminescent or reflective. In this manner, the light that is emitted from the water dispenser 10 (via the discharge outlet 14 or otherwise) and/or portions of the washbasin 11 itself, does not create background "noise" that would interfere with the user's ability to observe luminescence on his or her hands 50. For example, in one aspect of the technology, the washbasin 11 comprises a black surface configured to absorb light. With a washing area configured to be within a portion of the washbasin 11 itself, only the luminescent material present on the hands 50 of the user would luminesce. Advantageously, the user is better able to view and remove residual luminescent material. In addition, the light source 15 can be disposed about sides of the washbasin 11 in addition to or in lieu of placement of the light source 15 about the water dispenser 10. In this aspect, as with other aspects described herein, the light source 15 is oriented such that the light path 32 is not directed towards the eyes of the user. Rather, the light path 32 is oriented such that it resolves on the hands 50 of the user when placed within the washbasin 11.

In one aspect of the technology, the height of the discharge outlet 14 is placed so as to minimize inadvertent exposure of light to the eyes of the person. In this manner, visual inspection of the hands 50 is optimized. The person washing his or her hands 50 views the hands 50 from a position above the light source 15 to optimize hand washing and removal of residual luminescent materials. While reference is made herein to removal of luminescent materials from the hands 50 of the person, it is important to note that the luminescent marker present in the composition is intended to act as a surrogate measure of removal of other contaminants that may be present on the hands 50 by removal of the washing composition, be it soap, antiseptic, a combination of these or otherwise.

Figure 8:
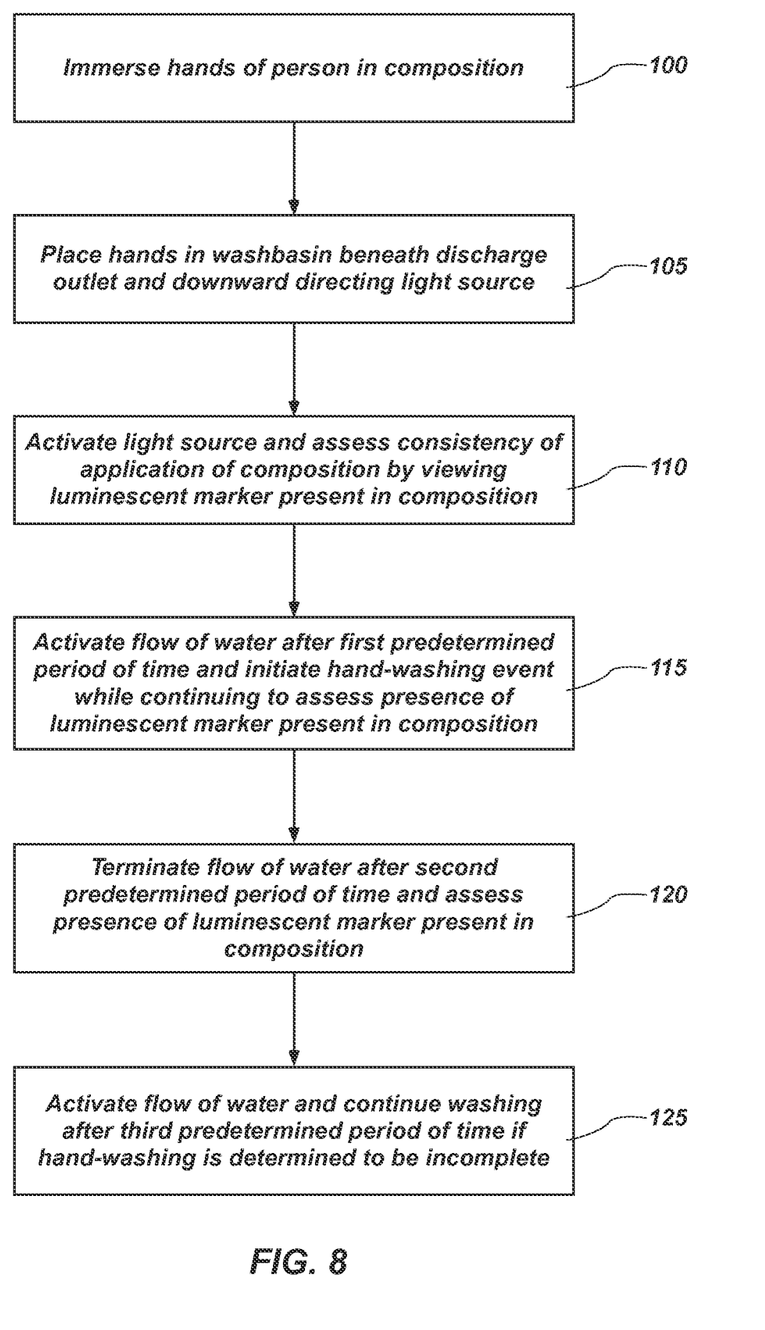
FIG. 8 is a flow chart illustrating certain aspects of the technology.

A method of hand washing incorporating concepts, devices, and compositions described herein forms part of the improvement to the current technology. With reference generally to FIG. 8, the method comprises providing a composition in a container with liquid therein comprising a marker capable of luminescence when exposed to radiation having a wavelength ranging from approximately 315 to 400 nanometers and immersing (or otherwise covering) 100% of the hands of the person in the composition for a predetermined period of time. That period of time depends on the composition used but may range, in one non-limiting example, from approximately 5 to 10 seconds. The method further comprises providing a water dispenser adapted to communicate water from a water source to the hands of a person. The water dispenser comprises a light source adapted to emit radiation when the hands of the user are placed within the washing area, for example, beneath the water source within a washbasin 105. In one aspect, the light source is configured to emit radiation having a wavelength ranging from approximately 315 to 400 nanometers. The light source is disposed about the water dispenser such that the light path of the light source is substantially the same as a direction of water dispensed from the water dispenser. Advantageously, the user may wash his or her hands while simultaneously observing the effectiveness of the handwashing due to the removal of the luminescent marker.

The sensor is configured to activate a light source when the hands of the user are disposed in the light path of the light source and discharge outlet of the water dispenser 110. A beam of light is emitted from the light source having a wavelength ranging, for example, from 315 to 400 nanometers for a predetermined period of time (e.g., 4 to 6 seconds, 5 to 10 seconds, etc.) to allow the user to examine the consistency of the composition disposed about his or her hands. However, frequencies of light greater than 400 nanometers may be used, and the period of time may be varied as suits a particular application. The method further comprises dispensing water from the water dispenser at the termination of the first predetermined period of time while washing the liquid from the hands of the person and maintaining the hands in the light from the light source 115. This step occurs for a second predetermined period of time (e.g., 1 to 2 minutes as suits a particular application) after which the water ceases to be dispensed 120. The method further comprises visually inspecting the hands of the person beneath the light source for traces of the luminescent marker agent. After a third predetermined period of time beneath the light source (e.g., 3 to 5 seconds), water is again dispensed for continued hand washing 125. This process is repeated until the user removes his or her hand from the field of view of the sensor which, ideally, occurs after all, or substantially all, of the composition is removed as evidenced by the lack of any luminescent marker present on the hands.

The foregoing detailed description describes the technology with reference to specific exemplary aspects. However, it will be appreciated that various modifications and changes can be made without departing from the scope of the present technology as set forth in the appended claims. The detailed description and accompanying drawings are to be regarded as merely illustrative, rather than as restrictive, and all such modifications or changes, if any, are intended to fall within the scope of the present technology as described and set forth herein.

More specifically, while illustrative exemplary aspects of the technology have been described herein, the present technology is not limited to these aspects, but includes any and all aspects having modifications, omissions, combinations (e.g., of aspects across various aspects), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus-function are expressly recited in the description herein. Accordingly, the scope of the technology should be determined solely by the appended claims and their legal equivalents, rather than by the descriptions and examples given above.

The invention claimed is:

1. A system for decontaminating a portion of a body, comprising:
    a composition comprising an agent capable of luminescence when exposed to radiation having a wavelength ranging from approximately 315 to 400 nanometers, wherein the composition is located in a container capable of facilitating application of the composition about the portion of the body;
    a fluid dispenser adapted to communicate fluid from a fluid source to the portion of the body; and
    a light source operative with the fluid dispenser, said light source oriented to emit light in a direction of the portion of the body when disposed beneath the fluid dispenser, wherein the light source is actuatable to emit radiation sufficient to cause the agent disposed about the portion of the body to luminesce.

2. The system of claim 1, wherein the portion of the body comprises the hands of a person and wherein the container is capable of receiving the hands of the person therein such that the hands are fully immersed in the composition.

3. The system of claim 1, wherein the light source is disposed about the fluid dispenser, said light source being adapted to emit radiation having a wavelength ranging from approximately 315 to 400 nanometers.

4. The system of claim 1, wherein the light source is disposed about a distal end of the fluid dispenser.

5. The system of claim 4, wherein the light source comprises a plurality of light sources disposed about a perimeter of the distal end of the fluid dispenser.

6. The system of claim 5, wherein the plurality of light sources is selected from the group consisting of a light emitting diode, an incandescent bulb, a fiber optic assembly, and any combination of these.

7. The system of claim 1, wherein the light source is disposed within a hollow body of the fluid dispenser.

8. The system of claim 7, wherein the light source is configured to emit light into a volume of the fluid being dispensed from the fluid dispenser, wherein the light is caused to at least partially pass through the volume of the fluid as it exits the fluid dispenser and contacts the hands of the person.

* * * * *